US008270250B2

(12) United States Patent
Bonavides et al.

(10) Patent No.: US 8,270,250 B2
(45) Date of Patent: Sep. 18, 2012

(54) PROGRAMMABLE DATA ACQUISITION FOR TUBULAR OBJECTS

(75) Inventors: Clovis Bonavides, Houston, TX (US); Batakrishna Mandal, Missouri City, TX (US)

(73) Assignee: Halliburton Energy Services, Inc., Houston, TX (US)

(*) Notice: Subject to any disclaimer, the term of this patent is extended or adjusted under 35 U.S.C. 154(b) by 1547 days.

(21) Appl. No.: 11/324,475

(22) Filed: Jan. 3, 2006

(65) Prior Publication Data

US 2007/0152054 A1    Jul. 5, 2007

(51) Int. Cl.
*G01V 1/00* (2006.01)
(52) U.S. Cl. ............................................ 367/69
(58) Field of Classification Search ............... 367/25, 367/35, 69, 95; 181/102–106; 340/853.1–856.4
See application file for complete search history.

(56) References Cited

U.S. PATENT DOCUMENTS

| | | | | |
|---|---|---|---|---|
| RE25,928 E | * | 12/1965 | Geyer | 367/33 |
| 3,668,619 A | | 6/1972 | Dennis | |
| 4,402,068 A | * | 8/1983 | Angehrn | 367/26 |
| 4,420,268 A | * | 12/1983 | Tsukamura et al. | 400/233 |
| 4,663,727 A | | 5/1987 | Saporito et al. | |
| 4,701,892 A | | 10/1987 | Anderson | |
| 4,837,753 A | | 6/1989 | Morris et al. | |
| 4,876,672 A | | 10/1989 | Petermann et al. | |
| 4,969,128 A | * | 11/1990 | Dennis et al. | 367/25 |
| 5,164,548 A | | 11/1992 | Angehrn | |
| 5,179,541 A | * | 1/1993 | Weido | 367/69 |
| 5,255,245 A | | 10/1993 | Clot | |
| 5,555,220 A | * | 9/1996 | Minto | 367/86 |
| 5,995,447 A | * | 11/1999 | Mandal et al. | 367/35 |
| 6,661,737 B2 | * | 12/2003 | Wisniewski et al. | 367/25 |
| 2005/0284659 A1 | * | 12/2005 | Hall et al. | 175/27 |

FOREIGN PATENT DOCUMENTS

| | | |
|---|---|---|
| EP | 1348954 A1 | 10/2003 |
| WO | WO-2007/120933 A2 | 10/2007 |

OTHER PUBLICATIONS

"International Application Serial No. PCT/US2007/060019, International Preliminary Report on Patentability mailed Mar. 26, 2008", 13 pgs.
"International Application Serial No. PCT/US2007/060019, International Search Report mailed Nov. 8, 2007", 4 pgs.
"International Application Serial No. PCT/US2007/060019, Written Opinion mailed Nov. 8, 2007", 7 pgs.
"European Application Serial No. 07777488.3, Office Action Response Filed Oct. 20, 2010", 13.

* cited by examiner

*Primary Examiner* — Jack W Keith
*Assistant Examiner* — Krystine Breier
(74) *Attorney, Agent, or Firm* — Schwegman Lundberg & Woessner, P.A.

(57) ABSTRACT

In some embodiments, apparatus and systems, as well as methods, may operate to select an amount of imaging coverage associated with a substantially tubular object and a rotary scanner coupled to a telemetry system. Determining circumferential and longitudinal scan sampling intervals to provide substantially full coverage of the substantially tubular object may be included. Waveform sampling and transducer driving waveform parameters may also be determined according to an available data transmission bandwidth associated with the telemetry system.

19 Claims, 5 Drawing Sheets

PROGRAMMABLE DATA ACQUISITION FOR TUBULAR OBJECTS

TECHNICAL FIELD

Various embodiments described herein relate to petroleum recovery operations, including apparatus, systems, and methods to improve the efficiency of ultrasonic data acquisition for inspection and imaging associated tubular components.

BACKGROUND INFORMATION

Images of well casings and other tubular drilling operation components, such as risers, may be constructed using waveform data acquired from transmitting and receiving ultrasound. In some systems, parameters such as the waveform acquisition time and sampling interval are fixed, resulting in either oversampling (for small objects) or undersampling (for large objects). Oversampling may produce in more data than is needed for complete coverage, while undersampling can lead to missed defects. Thus, a more flexible approach is needed to reduce inspection times, conserve the memory used to store acquired data, and still provide substantially complete coverage of the imaged object.

DETAILED DESCRIPTION

Figure 1A:
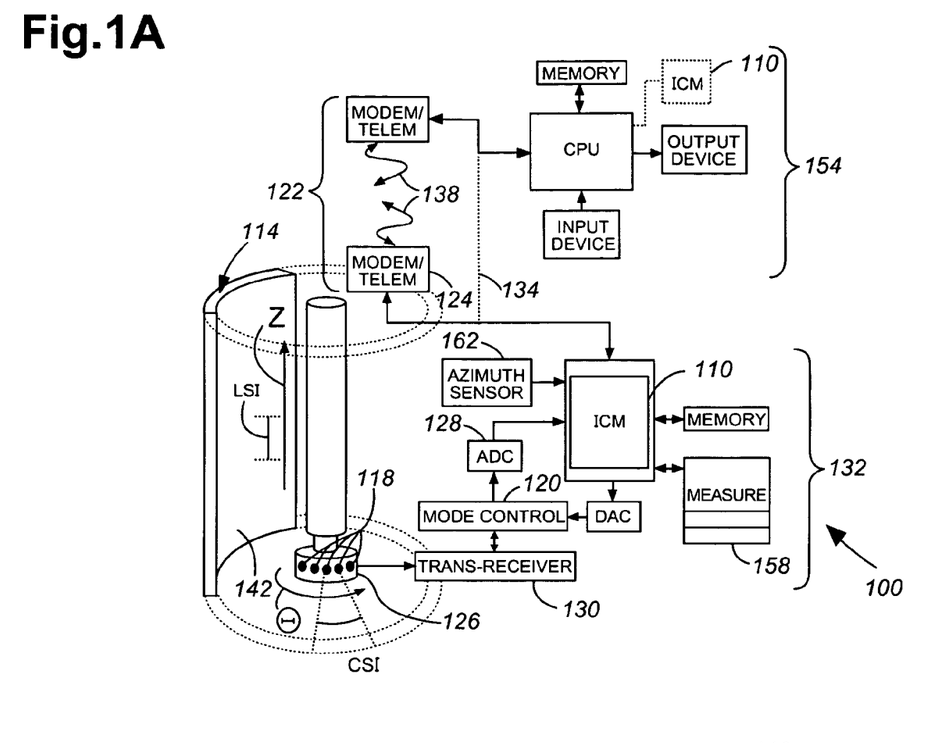
FIGS. 1A-1B illustrate an apparatus and an image coverage module, respectively, according to various embodiments of the invention.
Figure 1B:
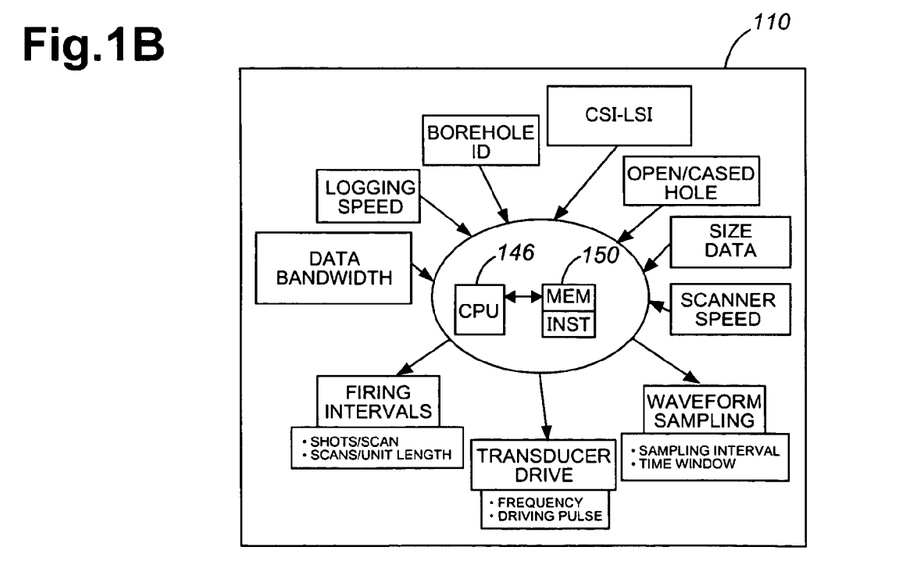

FIGS. 1A-1B illustrate an apparatus 100 and an image coverage module 110, respectively, according to various embodiments of the invention. Well casings, liners, risers, and other substantially tubular objects 114 can be inspected using one or more transducers 118 to transmit and receive ultrasonic waves that interact with the object 114 to be inspected. Images of an object 114 may be created using the acquired waveform data, usually stored as a series of digital samples. In some embodiments of the invention, the challenges described previously may be addressed by determining a circumferential scan sampling interval CSI and a longitudinal scan sampling interval LSI to provide substantially full coverage of the substantially tubular object 114. In addition, waveform sampling parameters and transducer driving waveform parameters may be determined according to a data transmission bandwidth, perhaps as part of a wireless communication system 122 used to transmit the acquired data to a remote location.

For example, an apparatus 100 may include a rotary scanner 126 and an imaging coverage module 110. The image coverage module 110 may operate to select an amount of imaging coverage associated with the substantially tubular object 114 and the rotary scanner 126.

The rotary scanner 126 may include an ultrasonic transreceiver 130 comprising a transmitter-receiver pair that may be electrically coupled to one or more transducers 118 included in the rotary scanner 126, perhaps using a multiplexer or some other switching arrangement to operate the transducers 118 in pulse-echo mode. The pitch-catch mode may also be utilized in some embodiments. Thus, the ultrasonic signal transreceiver 130 may be mechanically coupled to the rotary scanner 126, or be included in a separate data acquisition system 132.

The rotary scanner 126 may comprise a mechanical rotary scanner (where one or more transducers 118 are moved about the circumference θ as they are fired) or an electronic rotary scanner (where transducers 118 remain stationary while being excited in sequence around the circumference θ). The rotary scanner 126 may have a fixed or variable circumferential scanning speed, and may provide ultrasonic signal data directly to the imaging coverage module 110, or indirectly, via one or more transreceivers 130, a mode control module (e.g., pulse/receive switch or multiplexer) 120, and/or an analog-to-digital converter (ADC) 128.

In use, the rotary scanner 126 may be lowered down into (e.g., inserted into) and retrieved from a substantially tubular object 114, perhaps using a wire cable, as may be encountered in wireline service operations. In some embodiments, the rotary scanner 126 may be attached to a drill string for measurement-while-drilling (MWD) or logging-while-drilling (LWD) operations. Data and command information 138 can be sent to a remote location (e.g., a surface computer system 154) via wires 134 or using a wireless communication system 122, perhaps comprising a telemetry system, including a mud telemetry system. The telemetry system may include, for example, a telemetry transmitter 124 to transmit data 138 provided by the imaging coverage module 110.

While the rotary scanner 126 moves in the longitudinal direction Z within the substantially tubular object 114, the transreceiver 130 may be used to launch or fire acoustic signals into the object 114, and to receive signal waveforms that are reflected back to the scanner 126. The image (spatial) sampling rate for signals reflected from the tubular wall 142 of the object 114 depends of the rotation speed of the scanner 126, the transducer firing interval, and the longitudinal speed of the scanner 126.

For the purposes of this document, an image may be understood to comprise a map representing one or more properties of an object in space. Properties may include the reflectivity, thickness, and acoustic impedance of the object, or material located behind the object, among others. As noted above, images may be constructed from a collection of acquired ultrasonic waveform samples. Depending on a number of factors, including the size of the substantially tubular object 114, the size of the transducers 118, the transducer driving waveform type and frequency, among others, the image constructed from the recorded acoustic echoes (reflections) may represent an undersampled or oversampled version of the actual object.

The area covered by each ultrasonic pulse—or "shot"—depends on the characteristics of the transducer being used. Thus, the coverage area may vary widely between different transducer types and shapes. Oversampling occurs when there is overlap between the areas covered by adjacent shots. When data is oversampled, the amount of time required to transmit the data to other locations using telemetry or other measures is generally increased. Undersampling occurs when the area to be inspected is not fully covered by the imaging device, such that the recorded shots do not cover the whole area. In some embodiments, the image is neither oversampled nor undersampled. Rather, the image may comprise data resulting from a number of shots that cover the surface or volume of the object 114 in a substantially complete fashion, such that there are substantially no gaps in the coverage.

Therefore, depending on the application (e.g., detailed imaging, random inspection, etc.), more or less data may be collected. For substantially tubular objects 114, the data to be collected using a rotary scanner 126 may be expressed in terms of the number of shots per scan (e.g., the circumferential scan sampling interval CSI), the number of scans per unit length along the length of the object 114 (e.g., the longitudinal scan sampling interval LSI), and waveform sampling parameters, such as the length in time of the recorded wave (e.g., the waveform recording time), and the time interval between samples of the waveform (e.g., the waveform sampling interval). Along with transducer driving waveform parameters, such as the driving waveform type and driving waveform frequency, these six elements can be chosen in a judicious fashion to improve data acquisition efficiency. For example, by considering the substantially tubular object 114 size data, including diameter, wall thickness, and length, the amount of time required to acquire data may be reduced, while still maintaining substantially complete coverage of the surface and/or volume of the object 114.

As noted above, the image coverage module 110 may operate to select an amount of imaging coverage associated with the substantially tubular object 114 and the rotary scanner 126. The imaging coverage may be selected by determining a circumferential scan sampling interval CSI and a longitudinal scan sampling interval LSI to provide substantially full coverage of the substantially tubular object 114. In many cases, limitations on the available transmission bandwidth represent an acquisition bottleneck. The waveform sampling parameters and transducer driving waveform parameters may be selected according to the data transmission bandwidth, such that the volume of data resulting from ultrasound inspection activity over time does not go beyond that which can be transported using the available bandwidth.

For the purposes of this document, "imaging coverage" may comprise a fractional quantity representing the imaged area (or volume) as a percentage of the total area (or volume) available for inspection. This is sometimes also referred to as the probability of defect detection for defects that are larger than the transducer's spatial resolution, which may represent the minimum defect size (or material gap) that can be reliably distinguished over a uniform surface.

In some embodiments, the imaging coverage module 110 may include a processor 146 and a memory 150 having instructions INST stored therein which, when executed by the processor 146, cause the selection of an amount of imaging coverage associated with the substantially tubular object 114 and the rotary scanner 126. The amount of imaging coverage may be selected by determining, in the spatial domain, the circumferential scan sampling interval CSI and the longitudinal scan sampling interval LSI. The amount of imaging coverage may be selected by determining, in the time domain, the waveform sampling interval and the waveform recording time. The amount of imaging coverage may be selected by determining, in accordance with the driving waveform, the driving waveform frequency and the driving waveform type (e.g., broadband, narrowband, etc.).

Thus, the image coverage module 110 may operate to select the number of shots to provide substantially full coverage of the object 114 (either surface or volumetric) given the transducers 118 at hand. The circumferential scan sampling interval CSI and the longitudinal scan sampling interval LSI may be estimated first, and then the waveform sampling interval, waveform recording time, driving waveform frequency, and driving waveform type may be adjusted so that the available transmission bandwidth can accommodate the amount of data acquired. The imaging coverage module may also operate to determine a firing interval for the rotary scanner 126, perhaps mounted to a downhole tool, as described below. The firing interval may be based on the circumferential scan sampling interval CSI and the longitudinal scan sampling interval LSI, if desired. For example, the firing interval may coincide directly with each one of the circumferential interval points, or with every other one of the circumferential interval points, etc.

In some embodiments, the apparatus 100 may include a data acquisition system 132 to receive the circumferential scan sampling interval CSI and the longitudinal scan sampling interval LSI information from a surface computer 154. The data acquisition system 132 may receive data from other devices in addition to the transducers 118. For example, the apparatus 100 may include one or more measurement devices 158 (e.g., calipers) to transmit size data associated with the substantially tubular object 114 to the imaging coverage module 110. Size data may include pipe thickness, pipe inside diameter, and pipe length, for example. Other devices that may be used to provide data to the data acquisition system 132 include an azimuth sensor 162, perhaps housed by a downhole tool.

Any of the types of data shown in FIG. 1B may be acquired by the apparatus 100 in an automated fashion, such as by direct connection to a measuring device and other measures known to those of skill in the art. Thus, items such as the available bandwidth to transmit data, the logging speed (e.g., longitudinal movement speed), borehole identification information, the circumferential scan sampling interval CSI and the longitudinal scan sampling interval LSI information, whether the borehole is open or cased (in the case of petroleum recovery operations), pipe size data, scanner speed (e.g., circumferential scanning rate), waveform sampling data, transducer drive data, and firing interval may all be acquired by the apparatus 100.

Figure 2A:
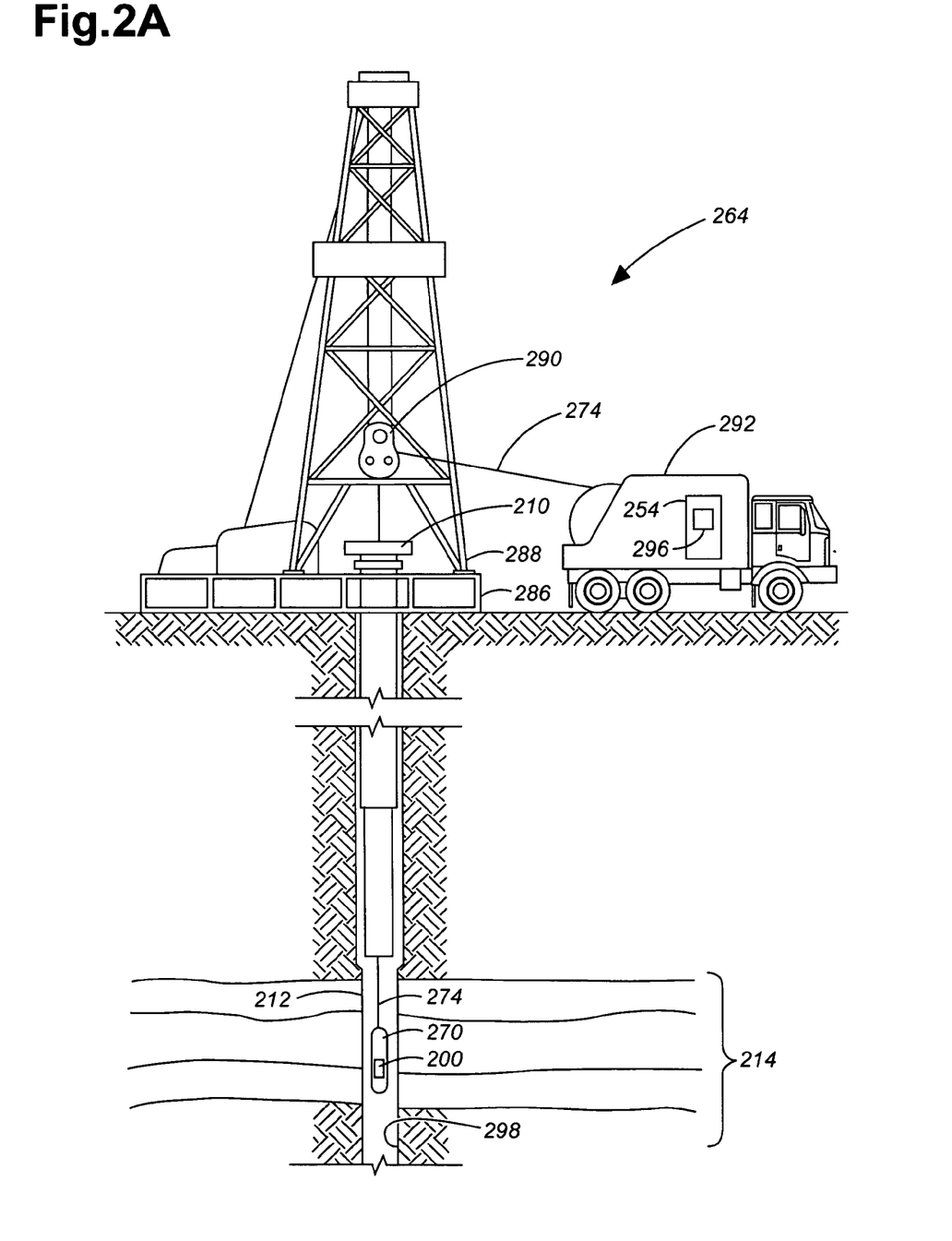
FIGS. 2A-2B illustrate apparatus and systems according to various embodiments of the invention.
Figure 2B:
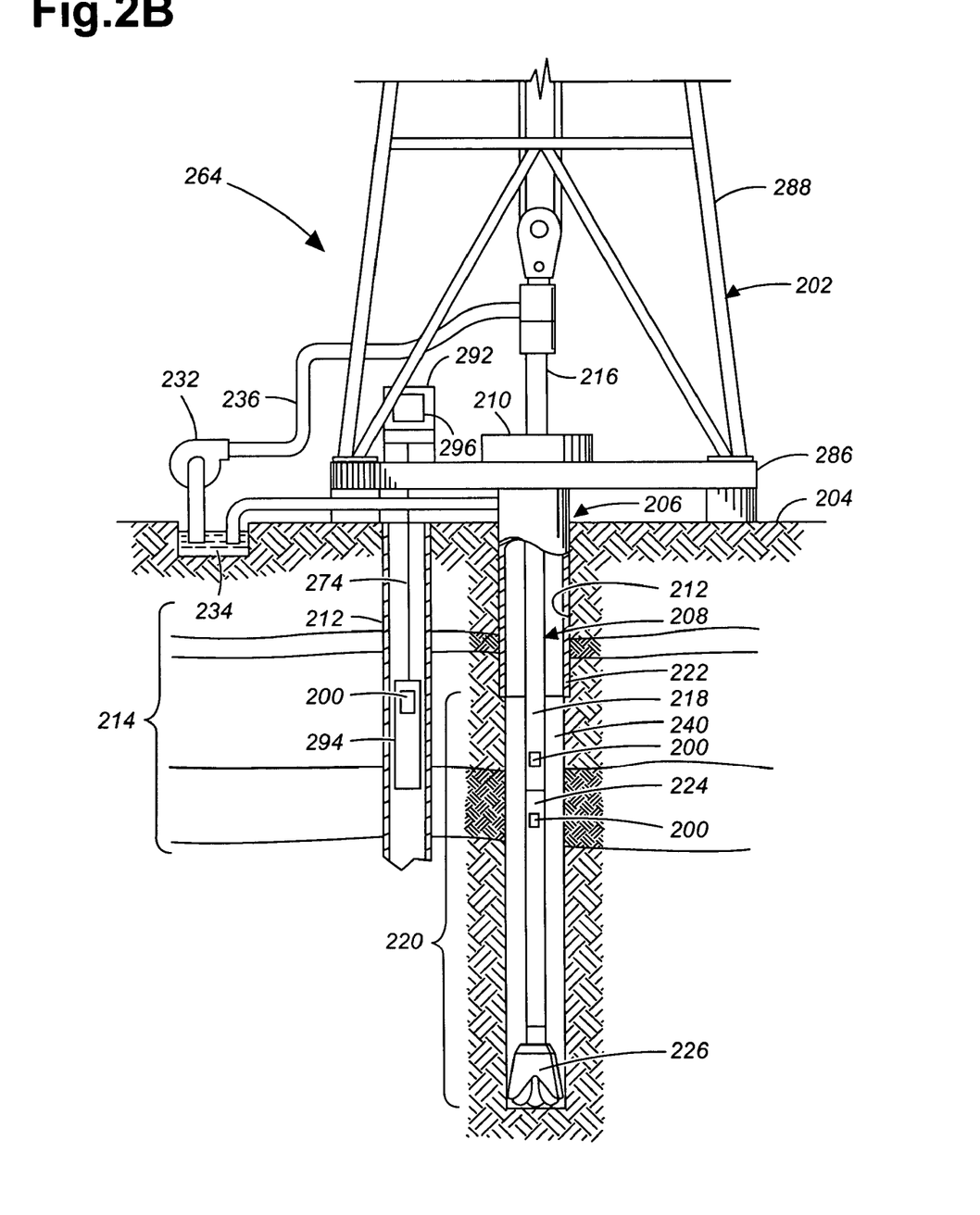

FIGS. 2A-2B illustrate apparatus 200 and systems 264 according to various embodiments of the invention. The apparatus 200, which may be similar to or identical to the apparatus 100 described above in FIG. 1A, may comprise portions of a tool body 270 as part of a wireline logging operation, or of a downhole tool 224 as part of a downhole drilling operation. For example, FIG. 2A shows a well during wireline logging operations. A drilling platform 286 may be equipped with a derrick 288 that supports a hoist 290. Drilling oil and gas wells is commonly carried out using a string of drill pipes connected together so as to form a drilling string that is lowered through a rotary table 210 into a wellbore or borehole 212. Here it is assumed that the drilling string has been temporarily removed from the borehole 212 to allow a tool body 270 (e.g., an MWD or LWD downhole tool), such as a probe or sonde, to be lowered by wireline or logging cable 274 into the borehole 212. Typically, the tool body 270 is lowered to the bottom of the region of interest and subsequently pulled upward at a substantially constant speed. During the upward trip, instruments included in the tool body 270 may be used to perform measurements on the subsurface formations 214 adjacent the borehole 212 as they pass by. The measurement data can be communicated to a logging facility 292 for storage, processing, and analysis. The logging facility 292 may be provided with electronic equipment for various types of signal processing. Similar log data may be gathered and analyzed during drilling operations (e.g., during LWD operations). For example, the tool body 270 in this case may house one or more apparatus 200, and the logging facility 292 may include one or more surface computers 254, similar to or identical to the surface computer 154 described above.

Turning now to FIG. 2B, it can be seen how a system 264 may also form a portion of a drilling rig 202 located at a surface 204 of a well 206. The drilling rig 202 may provide support for a drill string 208. The drill string 208 may operate to penetrate a rotary table 210 for drilling a borehole 212 through subsurface formations 214. The drill string 208 may include a Kelly 216, drill pipe 218, and a bottom hole assembly 220, perhaps located at the lower portion of the drill pipe 218. The drill string 208 may include wired and unwired drill pipe, as well as wired and unwired coiled tubing.

The bottom hole assembly 220 may include drill collars 222, a downhole tool 224, and a drill bit 226. The drill bit 226 may operate to create a borehole 212 by penetrating the surface 204 and subsurface formations 214. The downhole tool 224 may comprise any of a number of different types of tools including MWD tools, LWD tools, and others.

During drilling operations, the drill string 208 (perhaps including the Kelly 216, the drill pipe 218, and the bottom hole assembly 220) may be rotated by the rotary table 210. In addition to, or alternatively, the bottom hole assembly 220 may also be rotated by a motor (e.g., a mud motor) that is located downhole. The drill collars 222 may be used to add weight to the drill bit 226. The drill collars 222 also may stiffen the bottom hole assembly 220 to allow the bottom hole assembly 220 to transfer the added weight to the drill bit 226, and in turn, assist the drill bit 226 in penetrating the surface 204 and subsurface formations 214.

During drilling operations, a mud pump 232 may pump drilling fluid (sometimes known by those of skill in the art as "drilling mud") from a mud pit 234 through a hose 236 into the drill pipe 218 and down to the drill bit 226. The drilling fluid can flow out from the drill bit 226 and be returned to the surface 204 through an annular area 240 between the drill pipe 218 and the sides of the borehole 212. The drilling fluid may then be returned to the mud pit 234, where such fluid is filtered. In some embodiments, the drilling fluid can be used to cool the drill bit 226, as well as to provide lubrication for the drill bit 226 during drilling operations. Additionally, the drilling fluid may be used to remove subsurface formation 214 cuttings created by operating the drill bit 226.

Thus, referring now to FIGS. 1A-1B and 2A-2B, it may be seen that in some embodiments, the system 264 may include a drill collar 222, and a downhole tool 224, including a tool body 270 or a substantially permanently installed probe 294 (in a downhole well), to which one or more apparatus 200, are attached. The downhole tool 224 may comprise an LWD tool or MWD tool. The tool body 270 may comprise a wireline logging tool, including a probe or sonde, for example, coupled to a cable 274, such as a logging cable. Thus, a wireline 274 or a drill string 208 may be mechanically coupled to the downhole tool 224.

In some embodiments then, the system 264 may include a downhole tool 270 and an imaging coverage module 110, as described above and shown in FIG. 1B. The imaging coverage module 110, as well as an azimuth sensor 162, may be housed by the downhole tool 270. The system 264 may include a rotary scanner 126 attached to the downhole tool 270 to provide ultrasonic signal data 138 to the imaging coverage module 110. The system 264 may include one or more displays 296 to display defect data associated with the substantially tubular object, including pipe 298, such as well casing or well liners. The display 296 may be included as part of a surface computer 254 used to receive data 138 from the imaging coverage module 110, if desired.

The apparatus 100, 200; imaging coverage module 110; substantially tubular objects 114; transducers 118; wireless communication system 122; rotary scanner 126; ADC 128; ultrasonic transreceiver 130; data acquisition system 132; wires 134; data and command information 138; tubular wall 142; processor 146; memory 150; surface computers 154, 254; measurement devices 158; azimuth sensor 162; drilling rig 202; surface 204; well 206; drill string 208; rotary table 210; borehole 212; subsurface formations 214; Kelly 216; drill pipe 218; bottom hole assembly 220; drill collars 222; downhole tool 224; drill bit 226; mud pump 232; mud pit 234; hose 236; annular area 240; systems 264; tool body 270; cable 274; drilling platform 286; derrick 288; hoist 290; logging facility 292; probe 294; displays 296; pipe 298; circumferential scan sampling interval CSI; instructions INST; and longitudinal scan sampling interval LSI may all be characterized as "modules" herein. Such modules may include hardware circuitry, and/or a processor and/or memory circuits, software program modules and objects, and/or firmware, and combinations thereof, as desired by the architect of the apparatus 100, 200 and systems 264, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for drilling and logging operations, and thus, various embodiments are not to be so limited. The illustrations of apparatus 100, 200 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules, including multilayer, multi-chip modules. Such apparatus and systems may further be included as sub-components within a variety of electronic systems, such as process measurement instruments, personal computers, workstations, vehicles, and inspection systems for a variety of assemblies, among others. Some embodiments include a number of methods.

Figure 3:
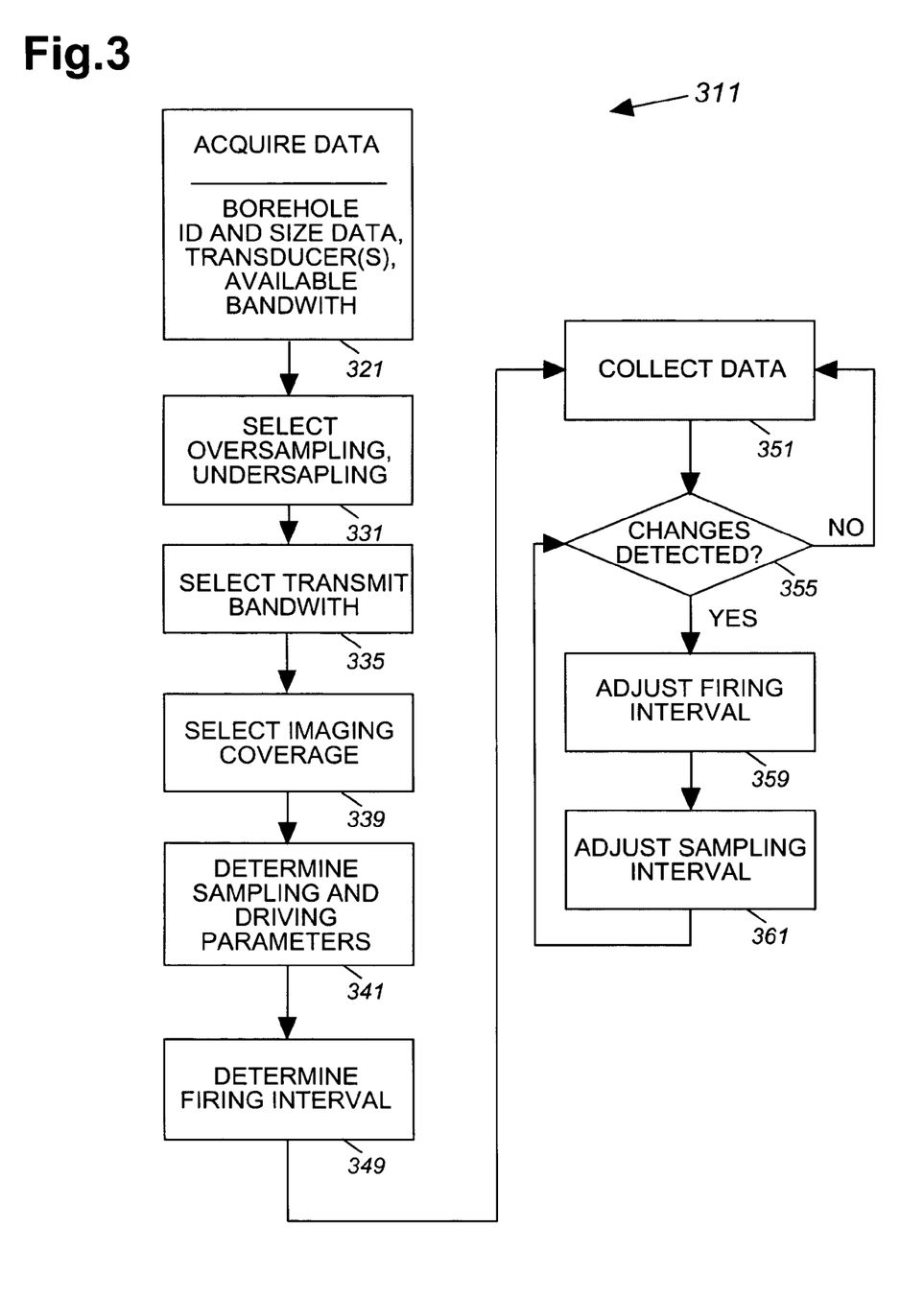
FIG. 3 illustrates a method flow diagram according to various embodiments of the invention.

For example, FIG. 3 illustrates a method flow diagram 311 according to various embodiments of the invention. In some embodiments, a method 311 may (optionally) begin at block 321 with acquiring various types of information or data, including acquiring borehole identification data associated with a substantially tubular object. Such information may comprise pipe outside diameter and pipe weight per-foot for a cased well, or bit size for an open (non-cased) hole. Size data associated with the substantially tubular object may include pipe thickness, pipe inside diameter, pipe outside diameter, and/or a pipe length.

Other activities for block 321 may include acquiring transducer characteristics for one or more transducers mounted to a rotary scanner, and acquiring an available data transmission bandwidth to transmit image data associated with the substantially tubular object. Information may therefore be acquired directly (e.g., via measurement devices or connecting cables), or indirectly. For example, pipe diameter and other parameters may be calculated based on ultrasonic data that has been acquired, either in real time, or from previous scan data. Information acquired as part of the activities for block 321 may therefore be acquired in real time and used to adjust other activities shown as part of the method 311, such as changing the logging speed (the speed of longitudinal movement in the substantially tubular object), changing the firing interval, and changing the scanner speed (the speed of circumferential rotation, either mechanical or electronic).

The method 311 may include selecting image oversampling operations or image undersampling operations at block 331, perhaps based on a selected application to provide a predetermined amount of imaging coverage. For example, undersampling may be chosen in the interest of saving examination time, memory, or money. Oversampling may be chosen based on a requirement to characterize very small defects, or according to specific regulations.

In some embodiments, the method 311 may include selecting a transmitting data bandwidth to transmit image data associated with the substantially tubular object at block 335. The transmitting data bandwidth may form a portion of the available data transmission bandwidth.

The method 311 may include, at block 339, selecting the amount of imaging coverage associated with a substantially tubular object and a rotary scanner coupled to a telemetry system by determining a circumferential scan sampling interval and a longitudinal scan sampling interval to provide substantially full coverage of the substantially tubular object. The method 311 may also include determining waveform sampling parameters and transducer driving waveform parameters according to the available data transmission bandwidth associated with a telemetry system at block 341. The method 311 may include, at block 349, determining a firing interval associated with the imaging coverage for a rotary scanner mounted in a downhole tool.

The method 311 may also include collecting data, such as image data, at block 351. If measurements are being made in real time, and changes are detected (e.g., the inside diameter or outside diameter of the tubular object changes by more than 10%) at block 355, then various adjustments may be made. If no changes are detected at block 355, then the method 311 may include continued data collection at block 351.

If changes are detected at block 355 (e.g., the speed of the rotating scanner changes, or the longitudinal speed of movement changes), the method 311 may include adjusting the firing interval based on the speed of rotation for the rotary scanner, or adjusting the firing interval based on the longitudinal speed of movement in the substantially tubular object, for example.

Other adjustments may be made. For example, if changes are detected at block 355 (e.g., the size data for the tubular object changes), the method 311 may include adjusting the circumferential scan sampling interval, the longitudinal scan sampling interval, the waveform sampling interval, or the waveform recording time based on the variation in the size data. It should be noted that the adjustments described with respect to blocks 359 and 361 may be implemented in response detecting other conditions, such as determining that the transducer is proximate to a particular location, or series of locations, along the longitudinal direction of the tubular object, or along the circumference of the object.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received, and perhaps stored using a variety of media, tangible and intangible, including one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 4:
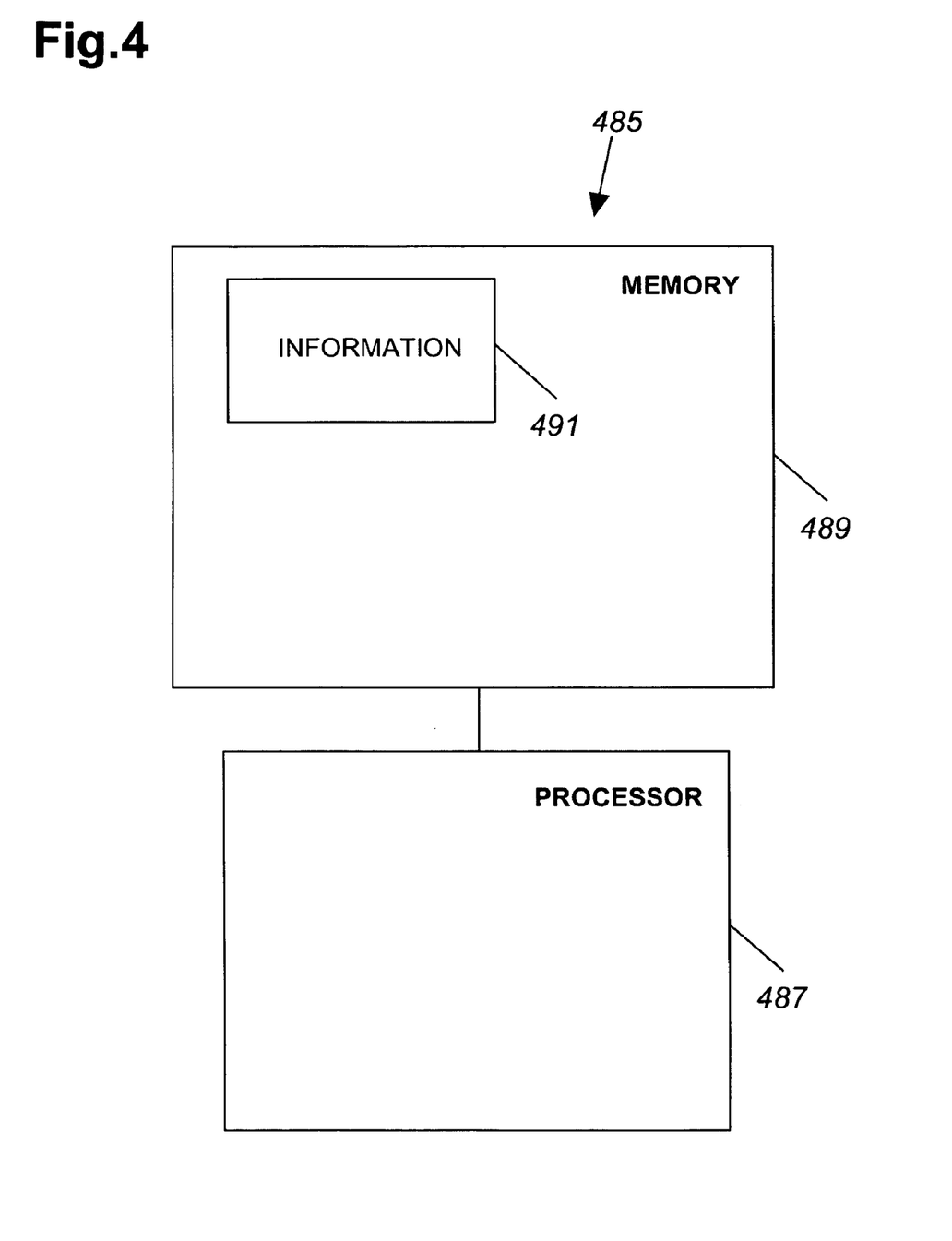
FIG. 4 is a block diagram of an article according to various embodiments of the invention.

FIG. 4 is a block diagram of an article of manufacture, or article 485 according to various embodiments, such as a computer, a memory system, a magnetic or optical disk, some other storage device, and/or any type of electronic device or system. The article 485 may include a processor 487 coupled to a computer-readable medium such as a memory 489 (e.g., fixed and removable storage media, including tangible memory having electrical, optical, or electromagnetic conductors; or even intangible memory, such as a carrier wave) having associated information 491 (e.g., computer program instructions and/or data), which when executed by a computer, causes the computer (e.g., the processor 487) to perform a method including such actions as acquiring size data associated with a substantially tubular object, and selecting an amount of imaging coverage associated with the substantially tubular object to a circumferential scan sampling interval, a longitudinal scan sampling interval, a waveform sampling interval, and/or a waveform recording time.

Other actions may include adjusting the circumferential scan sampling interval, the longitudinal scan sampling interval, the waveform sampling interval, or the waveform recording time based on a variation in the size data. Further actions may include determining a firing interval associated with the imaging coverage for a rotary scanner mounted in a downhole tool.

Implementing the apparatus, systems, and methods of various embodiments may promote more efficient data acquisition operations with respect to the inspection of sub-surface tubulars and wells, as well as other tubular structures. Increased efficiency may result in reduced data acquisition time, less costly inspection activities, and less memory used to store acquired data.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method, including:
selecting an amount of imaging coverage associated with a substantially tubular object and a rotary scanner coupled to a telemetry system by determining a circumferential scan sampling interval and a longitudinal scan sampling interval to provide substantially full coverage of the substantially tubular object, wherein selecting the amount of imaging coverage further includes selecting image undersampling based on a selected application to provide the amount of imaging coverage; and
determining waveform sampling parameters and transducer driving waveform parameters according to an available data transmission bandwidth associated with the telemetry system.

2. The method of claim 1, acquiring size data associated with a substantially tubular object, wherein the size data includes at least one of a pipe thickness, a pipe inside diameter, or a pipe length.

3. The method of claim 1, further including:
acquiring transducer characteristics for at least one transducer mounted to the rotary scanner.

4. The method of claim 1, further including:
acquiring the available data transmission bandwidth to transmit image data associated with the substantially tubular object.

5. The method of claim 1, further including:
selecting a transmitting data bandwidth to transmit image data associated with the substantially tubular object, wherein the transmitting data bandwidth forms a portion of the available data transmission bandwidth.

6. The method of claim 5, further including:
determining a firing interval associated with the imaging coverage for a rotary scanner mounted in a downhole tool.

7. The method of claim 6, further including:
adjusting the firing interval based on a speed of rotation for the rotary scanner.

8. The method of claim 6, further including:
adjusting the firing interval based on a longitudinal speed of movement in the substantially tubular object.

9. The method of claim 2, further including:
adjusting at least one of the circumferential scan sampling interval, the longitudinal scan sampling interval, a waveform sampling interval, or a waveform recording time based on a variation in the size data.

10. The method of claim 1, further including:
acquiring borehole identification data associated with the substantially tubular object.

11. The method of claim 1, further including:
receiving the circumferential scan sampling interval and the longitudinal scan sampling interval from a surface computer.

12. The method of claim 1, further including:
receiving size data associated with the substantially tubular object from a measurement device.

13. The method of claim 1, further comprising:
collecting image data associated with the substantially tubular object.

14. The method of claim 13, wherein the image data is collected from at least one transducer coupled electrically and/or mechanically to the rotary scanner.

15. The method of claim 13, further including:
transmitting the image data to a surface computer.

16. The method of claim 13, further including:
displaying the image data.

17. The method of claim 1, further including:
adjusting at least one of the circumferential scan sampling interval or the longitudinal scan sampling interval based on determining proximity to a particular location, or series of locations, along a longitudinal direction of the tubular object, or along a circumference of the object.

18. The method of claim 1, further including:
adjusting at least one of a waveform sampling interval or a waveform recording time based on determining proximity to a particular location, or series of locations, along a longitudinal direction of the tubular object, or along a circumference of the object.

19. The method of claim 1, further including:
selecting a transducer firing interval to coincide with selected circumferential interval points associated with the circumferential scan sampling interval.

* * * * *